United States Patent
Geddes (10) Patent No.: US 9,023,372 B2
(45) Date of Patent: May 5, 2015

(54) METAL-ENHANCED FLUORESCENCE NANOPARTICLES

(75) Inventor: Chris D. Geddes, Bel-Air, MD (US)

(73) Assignee: University of Maryland, Baltimore County, Baltimore, MD (US)

(*) Notice: Subject to any disclaimer, the term of this patent is extended or adjusted under 35 U.S.C. 154(b) by 1552 days.

(21) Appl. No.: 12/016,247

(22) Filed: Jan. 18, 2008

(65) Prior Publication Data

US 2009/0022766 A1 Jan. 22, 2009

Related U.S. Application Data

(60) Provisional application No. 60/950,492, filed on Jul. 18, 2007.

(51) Int. Cl.
| | |
|---|---|
| B32B 5/16 | (2006.01) |
| A61K 47/12 | (2006.01) |
| A61K 8/11 | (2006.01) |
| A61K 49/00 | (2006.01) |
| A61K 8/19 | (2006.01) |
| A61K 8/49 | (2006.01) |
| A61Q 1/02 | (2006.01) |
| A61Q 1/06 | (2006.01) |
| A61Q 1/08 | (2006.01) |
| A61Q 1/10 | (2006.01) |
| B82Y 5/00 | (2011.01) |

(52) U.S. Cl.
CPC ....... *A61K 49/0043* (2013.01); *Y10T 428/2991* (2015.01); *A61K 8/19* (2013.01); *A61K 8/498* (2013.01); *A61K 49/0021* (2013.01); *A61K 49/0041* (2013.01); *A61K 49/0093* (2013.01); *A61K 2800/413* (2013.01); *A61K 2800/434* (2013.01); *A61Q 1/02* (2013.01); *A61Q 1/06* (2013.01); *A61Q 1/08* (2013.01); *A61Q 1/10* (2013.01); *B82Y 5/00* (2013.01)

(58) Field of Classification Search
CPC ....... A01N 59/16; A01N 25/28; A01N 25/34; A01N 25/26; A01N 59/20; A61K 33/24; A61K 39/0011; A61K 45/06; A61K 47/48861; A61K 47/48884; A61K 9/14; A61K 2039/55516; A61K 2039/572; A61K 2039/60
USPC ......................................................... 424/401
See application file for complete search history.

(56) References Cited

U.S. PATENT DOCUMENTS

| | | | |
|---|---|---|---|
| 5,017,009 A | | 5/1991 | Schutt et al. |
| 5,324,494 A | * | 6/1994 | Glatzmaier .................. 423/345 |
| 5,449,918 A | | 9/1995 | Krull et al. |
| 5,866,433 A | | 2/1999 | Schalkhammer et al. |
| 6,417,340 B1 | * | 7/2002 | Mirkin et al. ................ 536/23.1 |
| 6,548,264 B1 | * | 4/2003 | Tan et al. ..................... 435/7.21 |
| 7,253,452 B2 | | 8/2007 | Steckel et al. |
| 7,348,182 B2 | | 3/2008 | Martin et al. |
| 7,351,590 B2 | | 4/2008 | Martin |
| 7,648,834 B2 | | 1/2010 | Moore |
| 7,718,445 B2 | | 5/2010 | Martin |
| 2003/0228682 A1 | | 12/2003 | Lakowicz et al. |
| 2004/0160606 A1 | | 8/2004 | Lakowicz et al. |
| 2006/0147927 A1 | | 7/2006 | Geddes et al. |
| 2007/0037215 A1 | * | 2/2007 | Patton ........................... 435/7.1 |
| 2007/0269826 A1 | | 11/2007 | Geddes |
| 2008/0096281 A1 | | 4/2008 | Geddes et al. |
| 2009/0022766 A1 | | 1/2009 | Geddes |

FOREIGN PATENT DOCUMENTS

| | | |
|---|---|---|
| WO | 89/09408 | 10/1989 |
| WO | WO2004/024191 | 3/2004 |
| WO | WO2006/074130 | 7/2006 |
| WO | WO2006/137945 | 12/2006 |
| WO | WO2006/138698 | 12/2006 |
| WO | WO2007/053201 | 5/2007 |
| WO | WO 2007/095527 | 8/2007 |
| WO | WO 2008/048221 | 4/2008 |
| WO | WO 2008/151247 | 12/2008 |

OTHER PUBLICATIONS

Mirkin et al. "Hybrid Nanoparticles with Block Copolymer Shell Structures" JACS (1999), 121, 462-463.*
Lakowicz, Joseph R. "Radiative decay engineering 5: metal-enhanced fluorescence and plasmon emission." Anal. Biochem., 337(2): 171-194, Feb. 15, 2005.*
"Studies on the attachment of DNA to silica-coated nanoparticles through a Diels-Alder reaction"; Nucleosides, Nucleotides, and Nucleic Acids, 24 (5-7): 1075-1079, 2005. M. Proupin-Perez and R. Cosstick; L.M. Liz-Marzan and V. Salgueinno-Maceira; M. Brust.*
Aslan K, Gryczynski I, Malicka J, Matveeva E, Lakowicz JR, Geddes CD (2005) Metal-enhanced fluorescence: an emerging tool in biotechnology. *Curr Opin Biotechnol* 16(1):55-62.
Malicka J, Gryczynski I, Kusba J, Lakowicz JR (2003) Effects of metallic silver island films on resonance energy transfer between Cy3 and Cy5-labeled DNA. *Biopolymers* 70:595-603.
Aslan K, Geddes CD (2005) Microwave-accelerated metal-enhanced fluorescence (MAMEF): A new platform technology for ultra-fast and ultra-bright assays. *Anal Chem* 77(24):8057-8067.
Aslan K, Huang J, Wilson GM, Geddes CD (2006) Metal-enhanced fluorescence-based RNA sensing. *J Am Chem Soc* 128:4206-4207.
Aslan K, Geddes CD (2006) Microwave-accelerated and metal-enhanced fluorescence myoglobin detection on silvered surfaces: Potential application to myocardial infarction diagnosis. *Plasmonics* 1(1):53-59.

(Continued)

*Primary Examiner* — Audrea Buckley
(74) *Attorney, Agent, or Firm* — Marianne Fuierer; Moore & Van Allen, PLLC (57) ABSTRACT

The present invention relates to nanoparticles comprising a metallic core with a surface coating, wherein the coating comprises at least an excitable radiative molecule attached thereto or impregnated therein, and wherein the excitable molecule is positioned at a sufficient distance from metallic core to enhance emissions when excited. The nanoparticles are included in compositions that may be used for surface coatings, cosmetics, assays, flow velocity measurements and targeting of tissue.

13 Claims, 9 Drawing Sheets

(56) References Cited

OTHER PUBLICATIONS

Aslan K, Badugu R, Lakowicz JR, Geddes CD (2005) Metal-enhanced fluorescence from plastic substrates. *J Fluores* 15(2):99-104.

Aslan K, Holley P, Geddes CD (2006) Metal-enhanced fluorescence from silver nanoparticle-deposited polycarbonate substrates. *J Mater Chem* 16(27):2846-2857.

Geddes CD, Parfenov A, Roll D, Fang J, Lakowicz JR (2003) Electrochemical and laser deposition of silver for use in metal-enhanced fluorescence. *Langmuir* 19(15):6236-6241.

Aslan K, Szmacinski H, Lakowicz JR, Geddes CD (2004) Metal-enhanced fluorescence solution-based sensing platform. *J Fluores* 14:677-679.

Geddes CD (2002) Optical halide sensing using fluorescence quenching: Theory, simulations and applications-a review. *Meas Sci Tech* 12:R53-R88.

Aslan K, Leonenko Z, Lakowicz JR, Geddes CD (2005) Annealed silver-island films for applications in metal-enhanced fluorescence: Interpretation in terms of radiating plasmons. *J Fluores* 15:643-654.

Kobayashi Y, Katakami H, Mine E, Nagao D, Konno M, Liz-Marzan LM (2005) Silica coating of silver nanoparticles using a modified Stober method. *J Coll Inter Sci* 283(2):392-396.

Bruchez, M., Jr.; Moronne, M.; Gin, P.; Weiss, S.; Alivisatos, A. P. *Science* 1998, 281, 2013-2016.

Michalet, X.; Pinaud, F.; Lacoste, T. D.; Dahan, M.; Bruchez, M. P.; Alivisatos, A. P.; Weiss, S. *Single Mol*. 2001, 2, 261.

Aslan, K.: Wu, M; Lakowicz, J; Geddes, CD. (2007) Fluorescent Core-Shell Ag@SiO2 Nanocomposites for Metal-Enhanced Fluorescence and Single Nanoparticle Sensing Platforms. J. Am. Chem. Soc. 2007 129:1524-25.

Aslan, K.: Wu, M; Lakowicz, J; Geddes, CD. (2007) Metal Enhanced Fluorescence Solution-based Sensing Platform 2: Fluorescent Core-Shell Ag@SiO2 Nanoballs. J. Fluoresc. 17:127-131.

Geddes CD, Aslan K, Gryczynski I, Malicka J, Lakowicz JR (eds) Radiative decay engineering, in topics in fluorescence in fluorescence spectroscopy. Kluwer Academic/Plenum Publishers, New York, USA, p. 405.

\* cited by examiner

METAL-ENHANCED FLUORESCENCE NANOPARTICLES

CROSS-REFERENCE TO RELATED APPLICATIONS

This application claims priority to U.S. Provisional Application No. 60/950,492 filed in the United States Patent and Trademark Office on Jul. 18, 2007, the contents of which are hereby incorporated by reference herein for all purposes.

GOVERNMENT RIGHTS IN INVENTION

Work related to the invention was conducted in the performance of a grant from National Center for Research Resources RR 008119. As a result of such contract, the U.S. Government has certain rights in the invention described herein.

BACKGROUND OF THE INVENTION

1. Field of the Invention

The present invention relates to nanostructures, and more particularly, to coated nanoparticles and their use in detection systems and/or fluorescence compositions wherein the nanoparticles are surface coated with a polymeric or oxide material having fluorophores, luminophores or chemiluminescent species contacting the surface coating.

2. Background of the Related Art

The use of fluorescent nanoparticles as indicators in biological applications such as imaging and sensing has dramatically increased since the 1990s.[14] Metal-Enhanced Fluorescence (MEF) is a powerful technology [1], where the interactions of fluorophores with metallic nanoparticles results in fluorescence enhancement, increased photostability, decreased lifetimes due to increased rates of system radiative decay, [2] reduced blinking in single molecule fluorescence spectroscopy [1], and increased transfer distances for fluorescence resonance energy transfer 93]. However, almost all of the MEF applications to date have been performed on 2-dimensional surfaces, where glass microscope slides [4-6] or plastics [7-8], are used as the primary substrates that feature the silver nanostructures deposited using either wet-chemistry [4-8], electrochemically [9] or lithographically.

Single-molecule fluorescence spectroscopy is the prime tool in single nanoparticle sensing, and it provides several advantages over ensemble measurements, such as, the elimination of averaging of the spectral properties over all members of the ensemble, which can reveal fundamental features otherwise masked in ensemble experiments.[15] Accordingly, the use of fluorescent core-shell nanocomposites with single-molecule fluorescence spectroscopy is likely to enhance the capability of single nanoparticle sensing.

SUMMARY OF THE INVENTION

The present invention relates to nanoparticles comprising a metallic core with a surface coating, wherein the coating comprises at least an excitable radiative molecule attached thereto or impregnated therein, and wherein the excitable molecule is positioned at a sufficient distance from metallic core to enhance emissions when excited.

In one aspect, the present invention relates to a metallic particle, such as a metallic sphere encompassed with a polymer or silica coating for positioning of at least fluorophores, luminophores or chemiluminescent species and wherein the fluorophores, luminophores or chemiluminescent species are directly attached to the coating or impregnated within the coating. The coating can be evenly distributed on the metallic sphere, in a pattern, or discontinuously distributed and having a thickness from about 2 nm to about 40 nm. The metallic sphere can be a solid metallic sphere or a core of one material that is coated with a metallic surface. Preferably the metallic sphere has a diameter ranging from about from about 2 nm to 150 nm and more preferably from about 20 to 100 nm.

The metallic sphere may be fabricated from any metal that enhances fluorescence and preferably, the metallic element is a noble metal such as silver, gold, platinum, aluminum, copper, zinc, palladium and composites thereof. The fluorophores, luminophores or chemiluminescent species may be evenly distributed, randomly or patterned within or on the coating encompassing the metallic sphere.

In another aspect, the fluorescent metallic nanospheres of the present invention may also be conjugated with at least one targeting moiety, attached to the polymeric or silica coating in combination with the fluorescent molecule, which is specific for a cancer- and/or pathogen-specific marker on a tumor. Upon administration to a subject in a pharmaceutically acceptable carrier, the metallic nanospheres will specifically bind to those cells and/or organisms that express the biological entity specific for the targeting moiety. The subject is then exposed to electromagnetic radiation at a frequency for excitation of the attached fluorescing molecule to be used for tracking of the movement of the nanospheres, attachment to the target cell, or to determine size of tumor.

In yet another aspect. the metallic nanospheres may further comprise a linker, wherein the linker attaches the targeting moiety to the coating of the nanospheres. In certain embodiments, the linker is selected from the group consisting of a lipid, a carbohydrate, a polysaccharide, a protein, a polymer, a glycoprotein, and a glycolipid.

Another aspect of the present disclosure relates to a composition comprising at least one fluorescent metallic nanoparticle comprising a metallic core, a surface coating positioned on the metallic core, at least a fluorophore or similar molecule that radiates electromagnetic energy upon excitation that is positioned on the surface coating or impregnated therein and positioned at a distance form the metallic core to enhance fluorescence emissions, and optionally a targeting moiety, a probe or a solubilizing agent to increase solubility of the nanosphere. The metallic core may be any geometric shape including spherical, elliptical, triangular, rod shape and the like.

In another aspect, where the metallic nanosphere of the present invention comprises a fluorophore and a targeting moiety both of which are directly linked to the surface coating of the metallic nanosphere, the method of fabrication comprises (a) contacting the surface coating of the metallic core with fluorophore and a targeting moiety, wherein the fluorophore and targeting moiety can be directly conjugate to the surface of the coating; and (b) isolating the conjugated nanosphere. The targeting moiety may include but is not limited to an antibody or fragment thereof, a protein or a fragment thereof, an antisense nucleic acid, a polypeptide, a peptide nucleic acid, or an oligonucleotide. The fluorophore and target moiety may be attached to the surface coating of the metallic nanosphere via a covalent or non-covalent bond, as long as the bond is sufficiently strong to maintain attachment to the surface coating.

In another aspect, the present invention relates to a cosmetic composition for application to skin or hair comprising a metallic nanoparticle, and preferably a nanosphere having a metallic core and a coating encompassing such metallic core, wherein the coating comprises at least one fluorescent molecule attached to the surface of the coating or impregnated therein and positioned at a distance from the metallic core sufficient to enhance fluorescence of the molecule, in combination with a cosmetically acceptable vehicle. Preferably, the metallic nanosphere has a diameter from about 2 nm to 150 nm and more preferably from about 20 to 100 nm. The thickness of the coating is generally the thickness to provide a distance wherein the fluorophore is from about 5 nm to about 100 nm from the metal surfaces to provide optimal enhancement of fluorescence signal. Preferable distances are about 5 nm to about 50 nm depending on placement of the fluorescent molecules including the use of a linker or whether it is impregnated into the coating. Thus, the thickness of the coating can be from about 5 nm to about 50 nm and more preferably from about 10 nm to 30 nm.

In a still further aspect, the present invention relates to a surface coating composition, such a paint composition, which forms a continuous or semi-continuous film comprising: metallic nanospheres having a metallic core and a coating encompassing such metallic core, wherein the coating comprises at least one fluorescent molecule attached to the surface of the coating or impregnated therein and positioned at a distance from the metallic core sufficient to enhance fluorescence of the molecule in combination with a polar or non polar solvent having a sufficiently low volatility as to being capable of producing the film. The composition may further include polymers to increase the surface coverability of the paint composition. Additional components may include pigments, dyes, optical brighteners, fungicides, mildewcides, surfactants, flow modifiers, thickeners, free flow stabilizers, anti-skin agents, anti-flocculants, and pH stabilizers.

In yet another aspect, the present invention relates to a color composition comprising a metallic nanosphere having a metallic core and a coating encompassing such metallic core, wherein the coating comprises at least one fluorescent molecule attached to the surface of the coating or impregnated therein and positioned a sufficient distance from the metallic core to enhance fluorescence of the molecule, and in combination with a cosmetically acceptable vehicle and optionally at least one colorant selected from the group consisting of inorganic pigments, natural colorants, synthetic organic monomeric colorants, synthetic organic polymeric colorants, and combinations thereof.

Inorganic pigments may be selected from the group consisting of iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide (white), and combination thereof.

In another aspect, the fluorescent metallic nanoparticles of the present invention may be used in velocimetry of turbulent flows including liquids, gas, liquid crystals, super cooled liquids and plasmas. The nanoparticles may further include an additional linked agent to the surface coating or metallic surface that provides for an increase of buoyancy of the nanoparticles. The path of the metallic nanoparticles and velocity can be easily monitored by tracing of the fluorescent molecule. Preferably, the fluorescent molecule attached to or impregnate in the surface coating and positioned a sufficient distance from the metallic surface to enhance fluorescence. The fluorescence molecules may be any intrinsic or extrinsic fluorescence molecule that upon absorption of selected electromagnetic energy emits a detectable signal including but not limited to Rhodamine 6G, Rhodmaine B, 4-(Dicyanomethylene)-2-methyl-6-(p-dimethylaminostyryl)-4H-pyran, 2,7 Dichlorofluorescein, Fluorescein, and combination thereof.

Other features and advantages of the invention will be apparent from the following detailed description, drawings and claims.

DETAILED DESCRIPTION OF THE INVENTION

The present invention provides for the interactions of fluorophores with silver nanoparticles results in fluorescence enhancement, an increased photostability, and a decreased lifetime due to increased rates of system radiative decay. The reduction in lifetime, in addition to an increase in fluorescence emission is particularly interesting for fluorescence based applications: where a 20-fold increase in intensity coupled with a 10-fold reduction in fluorophore-particle lifetime, provides for a ≈200-fold potential increase in overall particle detectability.

"Fluorophore," as used herein, means any substance that emits electromagnetic energy such as light at a certain wavelength (emission wavelength) when the substance is illuminated by radiation of a different wavelength (excitation wavelength). Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); Rhodamine 800 (Rh800), Eu-TDPA [Tris(dibenzoylmethane) mono(5-amino phenanthroline)europium], fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2[(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, A1 Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrirmidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivatives thereof.

Additionally, a fluorescent mineral may be attached to the coating encompassing the metallic core or impregnated into the coating wherein the minerals may include, but are not limited to, andalusite and chiastolite(aluminum silicate); amblygonite(basic lithium aluminum phosphorate); phenakite(beryllium silicate); variscite(hydrous aluminum phosphate); serpentine(basic magnesium silicate); amazonite(potassium aluminum silicate); amethyst(silicon dioxide); chrysoberyl(beryllium aluminum oxide); turquoise(copper-containing basic aluminum phosphate); colorless, yellow or pink tourmaline(borosilicate); amber(succinite/various resins); opal(hydrous silicon dioxide); cerussite (lead carbonate); fuchsite(potassium aluminum silicate); diopside(calcium magnesium silicate); ulexite(hydrous sodium calcium borate); aragonite (calcium carbonate); willemite(zinc silicate); dumortierite(aluminum borate silicate); scheelite(calcium tungstate); smithsonite(zinc carbonate); danburite(calcium boric silicate); benitoite(barium titanium silicate); fluorite(fluorospar); halite; axinite(calcium aluminum borate silicate); scapolite(sodium calcium aluminum silicate); kyanite(aluminum silicate); sphalerite(zinc sulphite); calcite (calcium carbonate); and petalite(lithium aluminum silicate).

Notably, if the coating that encompasses the metallic core has a porosity factor, the minerals can easily be included in such pores of the formed coating.

Another aspect of the present invention relates to the metallic cores being coated with a biodegradable or biocompatible material to render the nanoballs biocompatible if administered to a subject. As used herein, the term "biocompatible" relates to any synthetic or naturally occurring macromolecule, such as a lipid, carbohydrate, polysaccharide, protein, polymer, glycoproteins, glycolipids, etc., and methods of applying said biocompatible material, that can be used to coat the nanoballs to render it safe for in vivo use in a subject. The biocompatible material may be directly coated over the metallic surface or positioned over the first coating adjacent to the metallic core. Various methods of preparing lipid vesicles have been described including U.S. Pat. Nos. 4,235,871, 4,501,728, 4,837,028; PCT Application WO 96/14057, New RRC, Liposomes: A practical approach, IRL Press, Oxford (1990), pages 33-104; Lasic D D, Liposomes from physics to applications, Elsevier Science Publishers BV, Amsterdam, 1993; Szoka et al., Ann. Rev. Biophys. Bioeng. 9:467 (1980); Liposomes, Marc J. Ostro, ed., Marcel Dekker, Inc., New York, 1983, Chapter 1; Hope et al., Chem. Phys. Lip. 40:89 (1986); each of which is incorporated herein by reference.

Any lipid including surfactants and emulsifiers known in the art is suitable for use in making the inventive coated metallic nanospheres. The lipid component may also be a mixture of different lipid molecules. These lipids may be extracted and purified from a natural source or may be prepared synthetically in a laboratory. In a preferred embodiment, the lipids are commercially available. Lipids useful in coating the metallic core include natural as well as synthetic lipids. The lipids may be chemically or biologically altered. Lipids useful in preparing the inventive bioconjugated nanospheres include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcho-line; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-laury-1 ether; a surface active fatty acid, such as palmitic acid or oleic acid; fatty acids; fatty acid amides; sorbitan trioleate (Span 85) glycocholate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecylamine; acetyl palmitate; glycerol ricinoleate; hexadecyl sterate; isopropyl myristate; tyloxapol; poly(ethylene glycol)5000-phosphatidylethanolamine; and phospholipids. The lipid may be positively charged, negatively charged, or neutral. In certain embodiments, the lipid is a combination of lipids.

As stated above, the metallic core of the nanospheres of the present invention may be coated with a synthetic or naturally occurring polymer. Exemplary polymers useful in the present disclosure include, but are not limited to, polyesters, polyamides, polyethers, polythioethers, polyureas, polycarbonates, polycarbamides, proteins, polysaccharides, polyaryls, etc. The polymers useful in the coatings may include average molecular weights ranging from 100 g/mol to 100,000 g/mol, preferably 500 g/mol to 80,000 g/mol. Notably, the polymer may be a biodegradable polymer such as synthesized from monomers selected from the group consisting of D, L-lactide, D-lactide, L-lactide, D, L-lactic acid, D-lactic acid, L-lactic acid, glycolide, glycolic acid, hydroxybutyric acids, and malic acid.

In another embodiment the surface coating may be formed from an oxide containing compound or include an oxide containing compound. The oxide layer may be formed from a deposition technique, such as vapor deposition. The oxide layer coating may include at least one metal selected from the group consisting of Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $SiO_2$, $TiO_2$, $Fe_2O_3$, CuO, ZnO, $Y_2O_3$, $ZrO_2$, $Nb_2O_5$, $MoO_3$, $In_2O_3$, $SnO_2$, $Sb_2O_5$, $Ta_2O_5$, $WO_3$, PbO or $Bi_2O_3$. These metal oxides may be used alone or in combination with other types of coatings. Preferably, the oxide is a silicon oxide, more preferably, $SiO_2$. The vapor deposition of $SiO_2$ is a well established technique for the controlled deposition of a variety of substrates. For example, an Edwards Vapor deposition module allows the deposition of an inert coating of $SiO_2$.

As used herein, the term "targeting moiety" may include, but is not limited to, any molecule that has specificity to a marker expressed by a cell or pathogen, either extracellularly (e.g., on the cell surface or secreted by the cell) or intracellularly. In certain embodiments, the targeting moiety is specific for a tumor antigen or acts as a probe used in an assay. In other embodiments, the targeting moiety is specific for a pathogenic antigen. The targeting moiety may include, but are not limited to, antibodies and fragments thereof, haptens, polypeptides, oligonucleotides, anti-sense RNA, Peptide Nucleic Acids, proteins, chimeric and/or fusion proteins, and the like.

The targeting moiety may be attached to the surface of the coated nanosphere via a linker. The targeting moiety can be attached by any stable physical or chemical association to the surface coating directly or indirectly by any suitable means (e.g., covalent bond, noncovalent bond, electrostatic charge and the like).

Direct linking of the targeting moiety implies only that functional groups on the coating surface of the nanosphere and the targeting moiety itself serve as the points of chemical attachment. In such instances, the surface coating can be modified by functional organic molecules with reactive groups such as thiols, amines, carboxyls, and hydroxyl. The surface active reactants include, but are not limited to, aliphatic and aromatic amines, mercaptocarboxylic acid, carboxylic acids, aldehydes, amides, chloromethyl groups, hydrazide, hydroxyl groups, sulfonates and sulfates to accommodate such direct linkages.

The metallic nanosphere of the present invention may also comprise a linker that attaches the coated metallic nanosphere to the targeting moiety indirectly. The term "spacer" may also be used interchangeably as a synonym for linker. Linkers used in the present disclosure may include lipids, polypeptides, oligonucleotides, polymers, and the like.

In another embodiment the metallic nanospheres that have a fluorescent molecule connected thereto may be incorporated into any kind of vehicle that is normally used for cosmetic compositions. For example, the metallic nanospheres can be added to solutions, colloidal dispersions, emulsions (oil-in-water or water-in-oil), suspensions, powders, foundations, creams, lip creams, lotions, gels, foams, mousses, sprays and the like. Methodology for formulation of different vehicle types is well known in the art, and can be found for example in Remington's The Science and Practice of Pharmacy, 19th Edition, Volume II.

In one embodiment, the fluorescent metallic nanospheres may be used in a powdered cosmetic, such as a face powder, an eye shadow, and a blush. In another embodiment, the fluorescent metallic nanospheres may be used as part of a liquid cosmetic, such as a liquid foundation, eyeliner, mascara, concealer or blush. In addition, the fluorescent metallic nanospheres may be used in solid or semi-solid gel or stick products, such as lipsticks, lip glosses, cream lipsticks, lip or eye pencils, stick foundations, concealers or stick blushes.

Notably the fluorescent metallic nanospheres may be combined with other pigments or dyes. The additional color components can be either organic or inorganic. Examples of useful inorganic pigments include iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide(white) and mixtures thereof. Other useful pigments are pearlants such as mica, bismuth oxychloride and treated micas, such as titanated micas and lecithin modified micas.

The organic pigments include natural colorants and synthetic monomeric and polymeric colorants. Exemplary colorants include phthalocyanine blue and green pigment, diarylide yellow and orange pigments, and azo-type red and yellow pigments such as toluidine red, litho red, naphthol red and brown pigments. Polymeric colorants include nylon powder, polyethylene, and polyesters. The polyesters can include linear, thermoplastic, crystalline or amorphous materials produced using one or more diols and one or more dicarboxylic acids copolymerized with colorants. An exemplary list of cosmetically acceptable colorants can be found in the International Cosmetic Ingredient Dictionary and Handbook, 7th Edition, CTFA, 1997, pp. 1628-1630, the contents of which are incorporated herein by reference.

Excitation of the fluorescence molecules may include radiation energy in the visible light range, UV, microwave or ir range. Preferably in compositions used in the cosmetic field or paint field, the fluorescence molecule positioned near the metallic surface is excited by ambient light, such as sun light or indoor lighting. Depending on the use of the metallic nanostructures, the visible light range is idea for paint and cosmetic applications. Further, energy in the UV, ir and/or microwave range is acceptable for assays, targeting tumor tissue or velocity measurements. Other light sources may include arc lamps and lasers, laser diodes and light emitting diode source. Emission, if in the visible range will be easily detected and other ranges of emissions can be detected by devices well known in the art.

Preparation of Fluorescent Metallic Nanospheres

Figure 1:
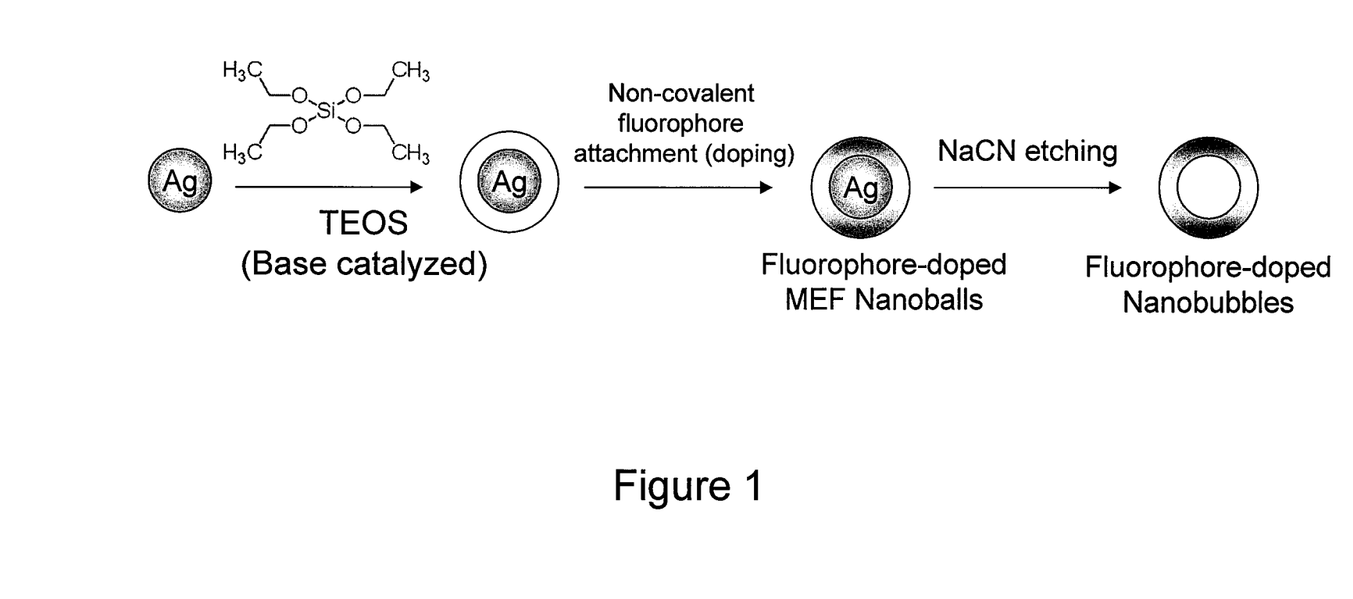
FIG. 1 is a schematic for the preparation of fluorescent core-shell Ag@$SiO_2$ (MEF) nanoballs and fluorescent nanobubbles.

The preparation of fluorescent core-shell Ag on $SiO_2$ nanoballs (MEF nanoballs) was undertaken in three steps (Figure 1) firstly, silver colloids are prepared by reduction of silver nitrate by sodium citrate, 2) then a silica shell of various thickness was grown around the colloids, and 3) lastly, fluorophore (Rh800) was doped into the silica shell. In order to show the benefits of using a silver core in the MEF nanoballs, fluorescent control probes were prepared without the silver core. The control fluorescent probes (without the silver core), named fluorescent nanobubbles, were prepared by dissolving the silver core away (etching) with cyanide from the fluorescent MEF nanoballs, c.f. FIG. 1. This procedure provided the best possible fluorescent control probes to evaluate the benefits of using a silver core: since the Rh800 employed here is hydrophobic [11] and retained in the hydrophobic pockets of the silica shell, the etching of the silver core with cyanide did not cause the removal of fluorophore from the shell (thickness≈10 nm). Thus, it is possible to compare the fluorescence emission of the fluorescent MEF nanoballs and of the fluorescent nanobubbles in a quantitative manner.

Materials and Reagent: Tetraethoxysilane (TEOS), (3-aminopropyl) triethoxylsilane (APS), were obtained from Sigma-Aldrich (St. Louis, Mo., USA). The fluorophores Alexa Fluor 647 (Alexa Fluor 647 labeling Kit), Rhodamine 800 (Rh800) and Eu-TDPA [Tris(dibenzoylmethane) mono (5-amino phenanthroline)europium] were obtained from Molecular Probes; Lambda Physik (Fort Lauderdale, Fla.), and Aldrich (St. Louis, Mo., USA), respectively.

Preparation of silver colloids: Silver colloids were prepared by adding dropwise 10 mL of 38.8 mM sodium citrate aqueous solution within 2 minutes to 490 mL of boiling aqueous solution containing 90 mg of AgNO$_3$ under vigorous stirring. After boiling for 10 minutes the solution was cooled to room temperature. The as-prepared silver colloid solution was centrifuged at 500 rpm for 1 hour to remove larger colloids, the remaining silver colloids in solution having an average size of ≈130 nm, as confirmed by TEM.

Single Molecule Fluorescence Spectroscopy (SMD): Single Alexa 647core-shell Ag@SiO$_2$ fluorescence measurements were obtained using a scanning confocal microscope (Picoquant MicroTime 200). The excitation laser was reflected by a dichroic mirror to a high numerical aperture (NA) oil objective (100×, NA 1.3) and focused to a diffraction limited spot (~300 nm) on the sample surface. Fluorescence emission from Alexa 647 core-shell Ag@SiO$_2$ was collected by an avalanche photodiode through the dichroic beam splitter and a band-pass (650-720 nm, Chroma) filter. Integration times of 3 ms per pixel were used to obtain 512×512 pixel raster scanned 20×20 μm images. The samples were excited with a 645 nm solid state laser.

Spectroscopic Measurements: Absorption spectra were measured on a Hewlett-Packard model 8543 spectrophotometer using 1-cm cuvettes. Steady-state fluorescence emission measurements were recorded with a Varian Eclipse spectrofluorometer. The fluorescence intensity decays were measured on a FluoroTime 200 (Picoquant GmbH, Berlin, Germany). Transmission electron micrographs (TEM) were taken with a side-entry electron microscope (Jeol Jem 1200 Ex II Microscope). Samples were cast from water solutions onto standard carbon-coated (200-300 Å) Formvar films on copper grids (200 mesh) by placing a droplet of a ca. 1 mg/mL aqueous sample solution on a grid, waiting 5 min, and removing excess solution by touching a small piece of filter paper to the edge of the grid. The grid was dried in air for 24 h. In some cases, ethanol solutions of the colloids were used and only 3 h were needed for drying.

Preparation of core-shell Ag@SiO$_2$ nanoballs: Under vigorous stirring, 1 mL of silver colloid solution was mixed with 250 mL of iso-propanol and 25 mL of deionized water. Immediately after the addition of 4 mL of 30% ammonium hydroxide, different amounts of TEOS were added to the reaction mixture. To obtain different silica layer thicknesses, 100 μl of the same amount of TEOS solution with a concentration between 50% and 100%, was added to the suspension. The reaction was stirred at room temperature for 30 minutes and then was allowed to age without agitation at 4° C. overnight. Each suspension of Ag@SiO$_2$ nanoballs was washed and centrifuged (at 3500 rpm for 30 min) three times with a water ethanol mixture (5:4) for 30 min, followed by resuspension in water. The thickness of the silica layers was determined from TEM images and varied from 2 to 35 nm, depending on the preparation parameters. The size of Ag colloids, the thickness of the silica shell and the change in absorbance of the Ag@SiO$_2$ particles. Δλmax is the difference between the λmax of Ag@SiO$_2$ and Ag colloids themselves, as shown below in Table 1

TABLE 1

|  | Silica Shell (nm) | Ag (nm) | Absorbance (λmax, nm) | Δλmax, nm |
|---|---|---|---|---|
| Ag colloids | — | — | 426 | — |
| A | 35 ± 1 | 130 ± 10 | 470 | 44 |

TABLE 1-continued

|  | Silica Shell (nm) | Ag (nm) | Absorbance (λmax, nm) | Δλmax, nm |
|---|---|---|---|---|
| B | 15 ± 1 | 130 ± 10 | 443 | 17 |
| C | 11 ± 1 | 130 ± 10 | 443 | 17 |
| D | 2 ± 1 | 130 ± 10 | 425 | 1 |

Preparation of the Fluorescent MEF Nanoballs:

Several methods have been developed for the coupling of fluorophores to the core-shell Ag@SiO$_2$.

One approach is through dyeing (doping) of the Ag@SiO$_2$ colloids. In this regard, 500 μl ethanol solution of 0.16 mg/ml Eu-TDPA or 0.088 mg/ml Rh800 was added into 500 μl (0.2 mg) of Ag@SiO$_2$ nanoparticles suspended solution and incubated overnight. The mixture was centrifuged and washed with 1.5 ml H$_2$O and 1.2 ml ethanol 4 times, respectively. The absorbance and the fluorescence spectra of the washing solution were monitored to ensure the complete removal of the unadsorbed fluorophores. For the nanobubbles with fluorophores, cyanide solution was added before the ethanol washing step and both fluorescent Ag@SiO$_2$ and nanobubbles followed the exact same procedure. The etching of the silver core with cyanide did not cause the removal of fluorophores from the shell thickness>10 nm but resulted in removal of most of the fluorophores from a 2 nm shell.

Another approach is through surface derivation and consequent covalent conjugation of fluorophores. In this regard, 1 mg of Ag@SiO$_2$ nanoparticles was washed consecutively with ethanol, ethanol-toluene (1:1), and toluene, before 20 mL of toluene and 1.6 g of APS was added. The mixture was refluxed for 24 h under nitrogen gas. Then, the nanoparticles were centrifuged and were washed with ethanol and water. A fraction of the above amino-derived nanoparticles was suspended in 1 mL of 0.1 M NaHCO$_3$ (pH 9.0,) and a solution of amino-active fluorophore, Alexa Fluor 647 in 500 μl DMSO, was added dropwise with stirring. After being stirred at room temperature overnight, the fluorescent core-shell Ag@SiO$_2$ nanocomposites were centrifuged and washed with water and ethanol, and then stored at 4° C. for further applications.

Still further, the fluorescent MEF nanoballs were prepared by dyeing (doping) of the Ag@SiO$_2$ nanoballs. 500 μl ethanol solution, 0.088 mg/ml Rh800, was added to 500 μl (0.2 mg) of Ag@SiO$_2$ nanoballs suspended solution and incubated overnight. The mixture was centrifuged and washed with 1.5 ml H$_2$O and 1.2 ml ethanol 4 times, respectively. The absorbance and the fluorescence spectra of the washing solution were monitored to ensure the complete removal of the unadsorbed fluorophores.

Figure 8:
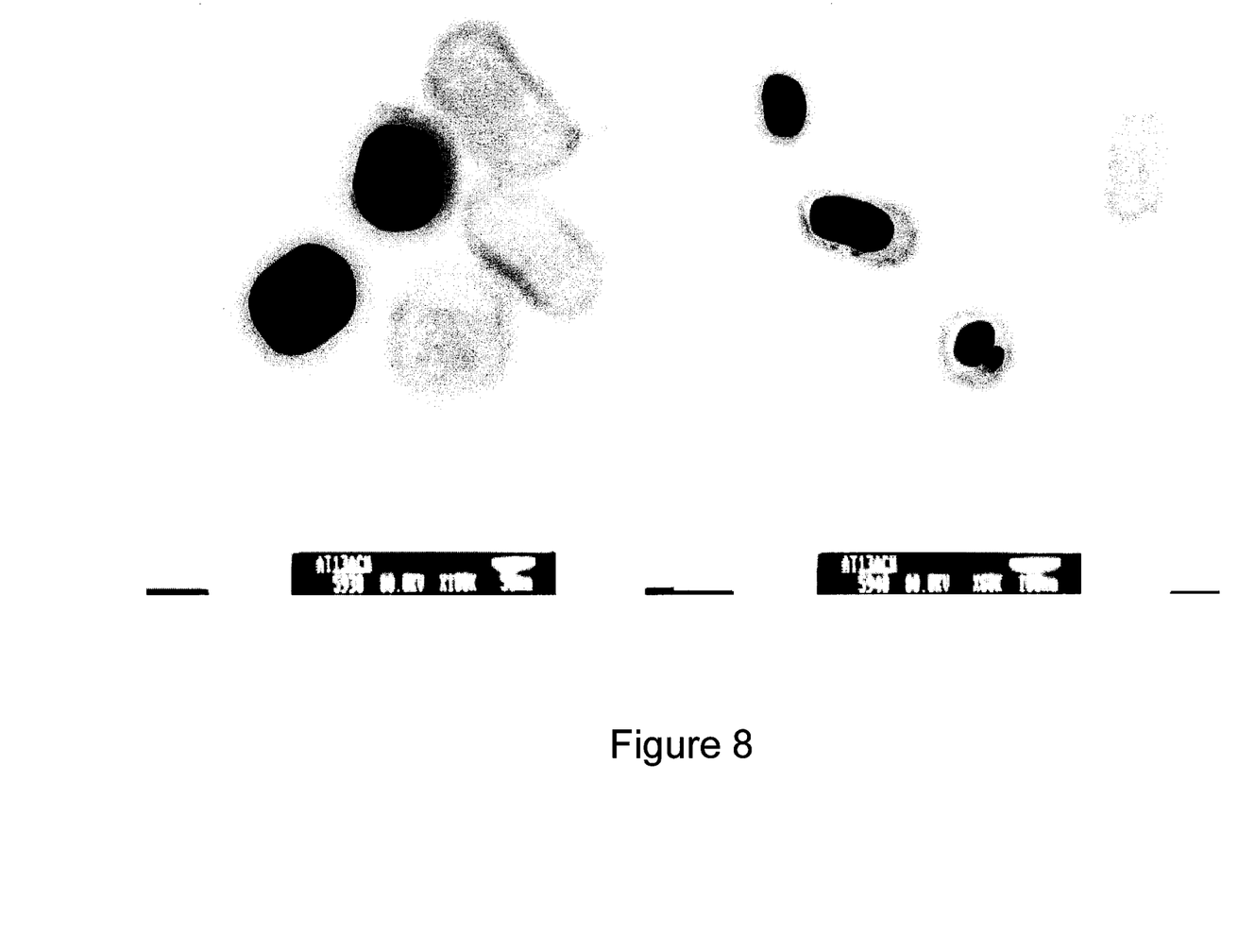
FIG. 8 shows TEM images of core-shell Ag@$SiO_2$ nanoparticles and nanobubbles.

Preparation of the nanobubbles from the MEF nanoballs: The nanobubbles prepared from the fluorescent MEF nanoballs were obtained using the following procedure. 500 μl of 0.1M sodium cyanide solution was added to an aged suspension of 200 μl of MEF nanoballs with agitation overnight to dissolve the silver core of the particles. Each suspension of MEF nanoballs/nanobubbles was washed and centrifuged three times with 1.5 ml water and 1.2 ml ethanol with sonication to remove unreacted ions at the final stage of preparation, followed by a final resuspension in water. FIG. 8 shows TEM images of nanobubbles.

The preparation of MEF nanoballs included several different ones with different thickness of the SiO$_2$ coating. The diameter of the silver core was 130±10 nm for all the preparations, a size which has been shown most suitable for MEF and the Radiating Plasmon Model [12]. The thickness of the silica shell was varied from 2 to 35±1 nm, to optimize fluorescence enhancement (data not shown) and was controlled by the concentration of TEOS after alkaline initiation.

Figure 2:
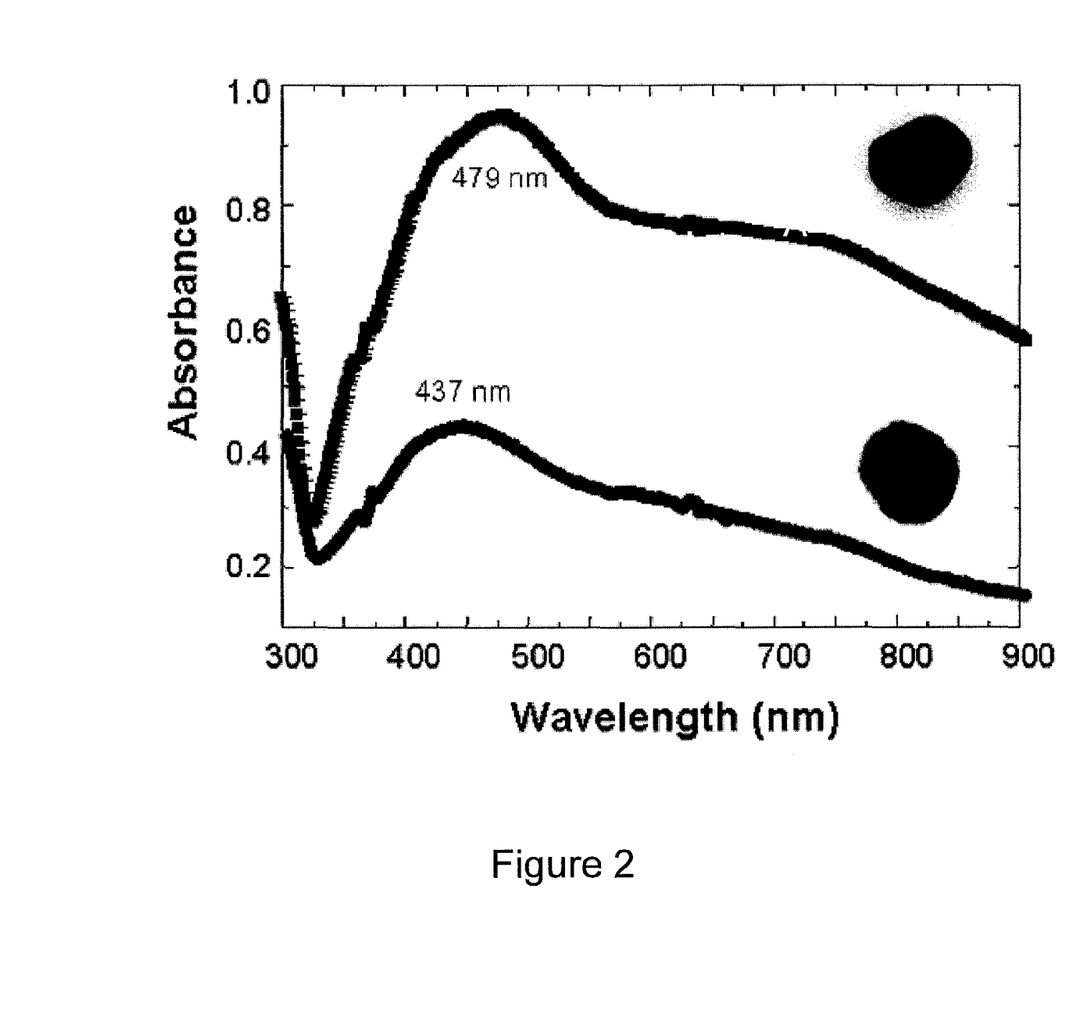
FIG. 2 shows the absorption spectra of two core-shell Ag@$SiO_2$ nanoballs with different shell thicknesses. Inset-TEM images of Ag@$SiO_2$ nanoballs. The diameter of the Ag is ≈130±10 nm and the thickness of the shell is A=35±1 nm, B=2±1 nm. The scale bar is obtained from the TEM images

FIG. 2 shows the absorption spectra of two MEF nanoballs with different shell thicknesses. Absorption spectra were measured on a Hewlett-Packard model 8543 spectrophotometer using 1-cm cuvettes. Steady-state fluorescence emission measurements were recorded using a Varian Eclipse spectrofluorometer. Transmission electron micrographs (TEM) were taken with a side-entry electron microscope (Jeol Jem 1200 Ex II Microscope). Samples were cast from water solutions onto standard carbon-coated (200-300 Å) Formvar films on copper grids (200 mesh) by placing a droplet of a ca. 1 mg/mL aqueous sample solution on a grid, waiting 5 min, and removing excess solution by touching a small piece of filter paper to the edge of the grid. The grid was dried in air for 24 h. In some cases, ethanol solutions of the colloids were used and only 3 h was needed for drying.

The surface plasmon resonance (SPR) peak of the silver shifted towards longer wavelengths as the thickness of the silica shell increased, as expected, and indeed observed by others [13]. The SPR peak of the MEF nanoballs with 2 and 35 nm shell thickness were observed at 437 and 479 nm, respectively. The nanobubbles however, show no plasmon absorption band, as the silver has been etched away by cyanide (data not shown). The importance of using the silica shell around the silver core is 3-fold: 1) silica layers offer the robustness, chemical inertness and the versatility needed for the conjugation of biomolecules or fluorophores; 2) it protects the silver core from ions present in biological media and 3) it allows for the distance dependent MEF phenomenon, which was determined for optimum for shell thicknesses to be <11 nm 1]. This thickness value is also consistent with values obtained from planar surfaces [1-10].

Figure 3:
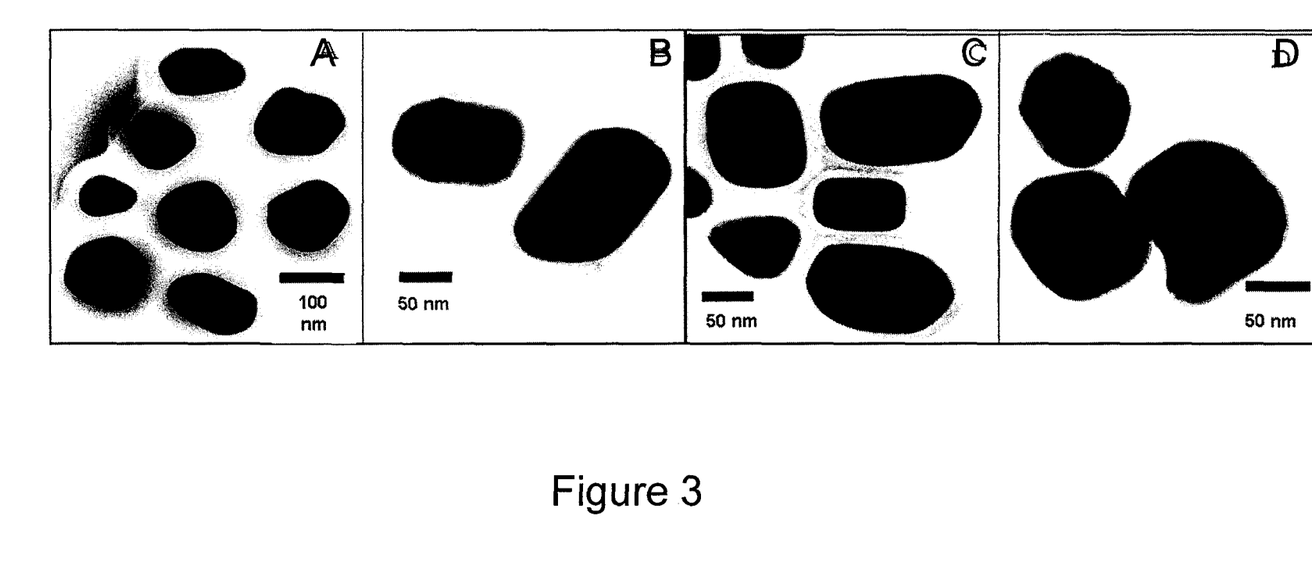
FIG. 3 shows the TEM images of Ag@$SiO_2$. Panels A, B, C, and D show the samples with different thickness of the $SiO_2$ coating at 35, 15, 11, and 2 nm (±1 nm), respectively. The diameter of the Ag is 130±10 nm for all the samples.

FIG. 3 shows the TEM images of core-shell $Ag@SiO_2$ nanocomposites with different thickness of the $SiO_2$ coating. The diameter of the silver core was 130±10 nm for all the preparations, a size which has been shown suitable for MEF and the radiating plasmon model. The thickness of the silica shell was varied from 2 to 35±1 nm, to optimize fluorescence enhancement and was controlled by the concentration of tetraethoxysilane (TEOS) after alkaline initiation. The surface plasmon resonance peak for silver shifted toward longer wavelengths as the thickness of the silica shell increased, as shown in Table 1, as expected and observed by others.[13] The importance of using the silica shell around the silver core is 3-fold: (1) silica layers offer the robustness, chemical inertness, and the versatility needed for the conjugation of biomolecules or fluorophores, (2) it protects the silver core from ions present in biological media, and (3) it allows for the distance dependent MEF phenomenon, which was determined for optimum for shell thicknesses to be <10 nm.[12]

Figure 4:
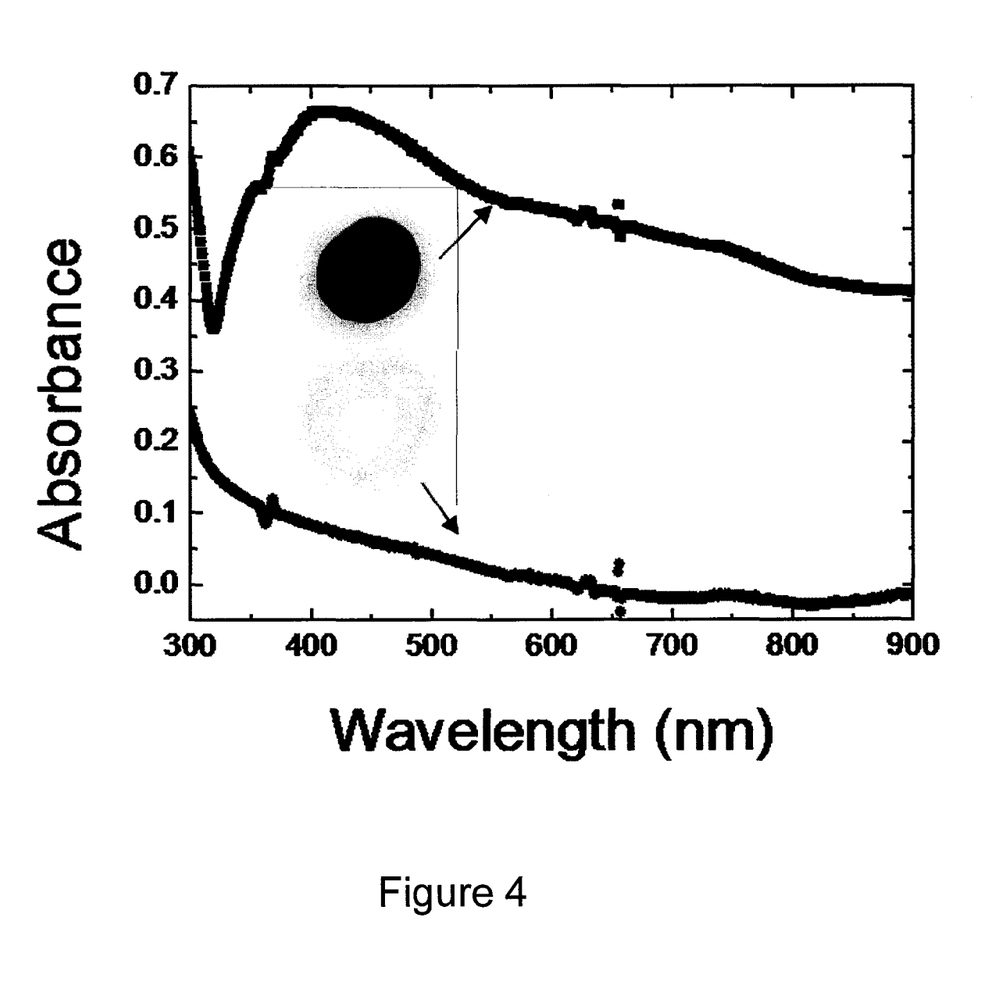
FIG. 4 shows the absorption spectra of core-shell Ag@$SiO_2$ nanoparticles and nanobubbles. The nanobubbles show no plasmon absorption band, as the silver has been etched away by cyanide.

FIG. 4 shows the absorption section of core-shell $Ag@SiO_2$ nanoparticles and nanobubbles. The nanobubbles show no plasmon absorption band, as the silver has been etched away by cyanide.

Figure 5:
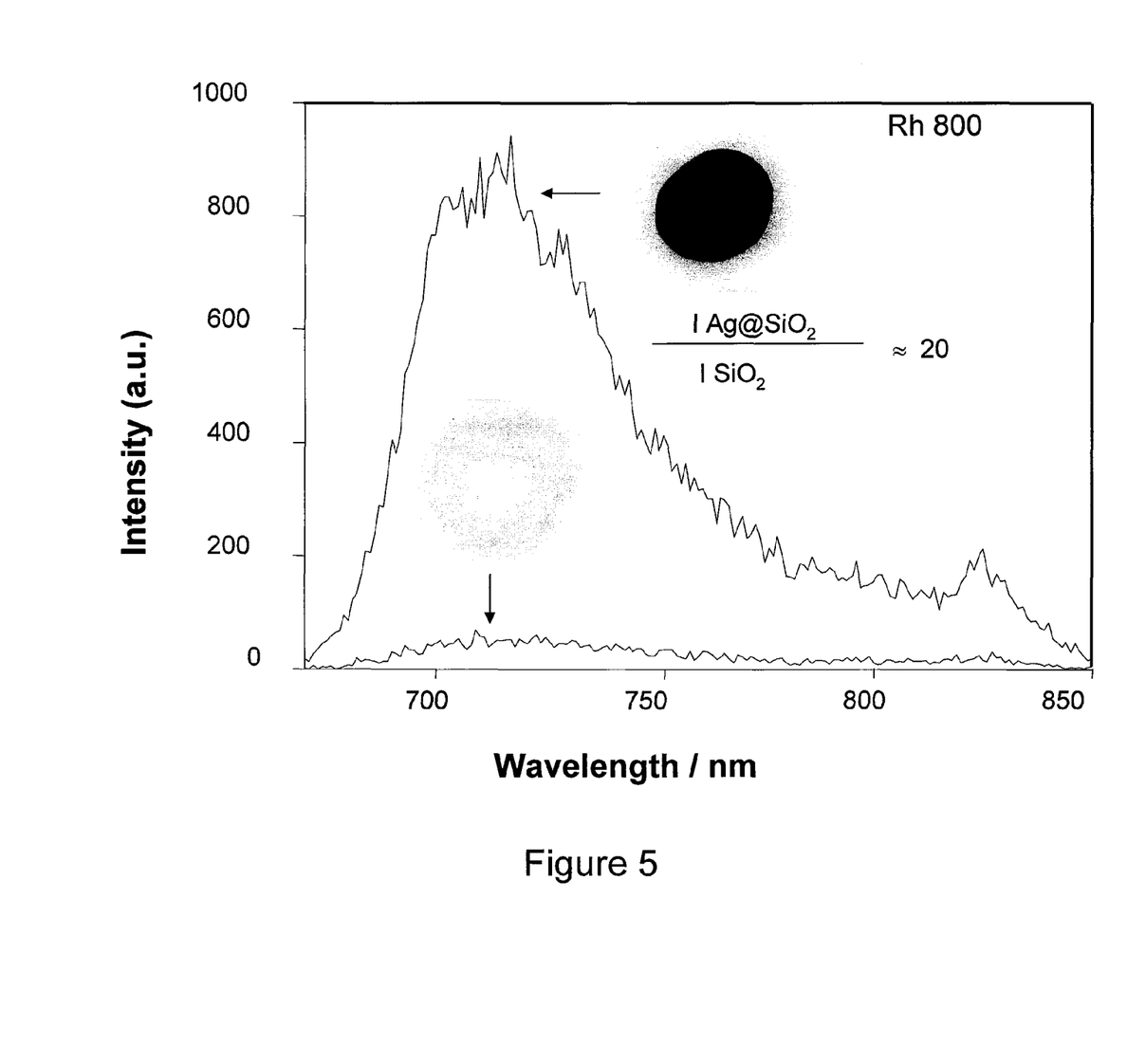
FIG. 5 shows the fluorescence emission spectrum of Rh800-doped MEF nanoballs and from the corresponding fluorescent nanobubbles (control sample, cyanide etched), Rh800-doped nanobubbles. The thickness of the shell is 11±1 nm (optimized with respect to maximum emission intensity) for all the samples

FIG. 5 shows the fluorescence emission intensity from Rh800-doped MEF nanoballs and from the corresponding fluorescent nanobubbles (control samples) Rh800-doped nanobubbles. The emission intensity was approximately 20-fold higher for Rh800-doped MEF nanoballs than Rh800-doped nanobubbles. The fluorescence emission spectra of the fluorophores were identical in both cases, indicating that the spectral properties of the fluorophores were retained.

Figure 6:
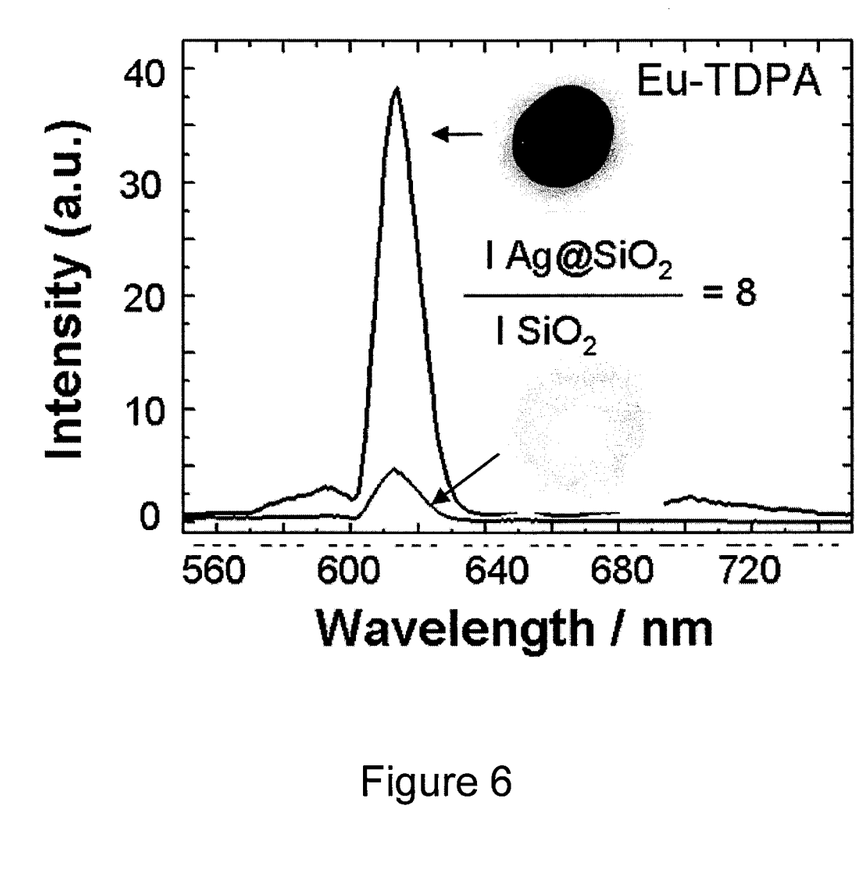
FIG. 6 shows the fluorescence emission spectrum of Eu-TDPA doped MEF nanoballs and from the corresponding fluorescent nanobubbles (control sample, cyanide etched), Eu-TDPA doped nanobubbles. The diameter of the Ag is 130±10 nm and the thickness of the shell is 11±1 nm for all samples.

FIG. 6 shows the fluorescence emission intensity from Eu-TDPA-doped $Ag@SiO_2$ and from the corresponding fluorescent nanobubbles (control samples), Eu-TDPA-doped $SiO_2$. The emission intensity was approximately 8-fold higher for Eu-TDPA-doped $Ag@SiO_2$ than for Eu-TDPA-doped $SiO_2$ Notably, the fluorescence emission spectra of the fluorophores were identical in both cases, indicating that the spectral properties of the fluorophores were retained.

Figure 9:
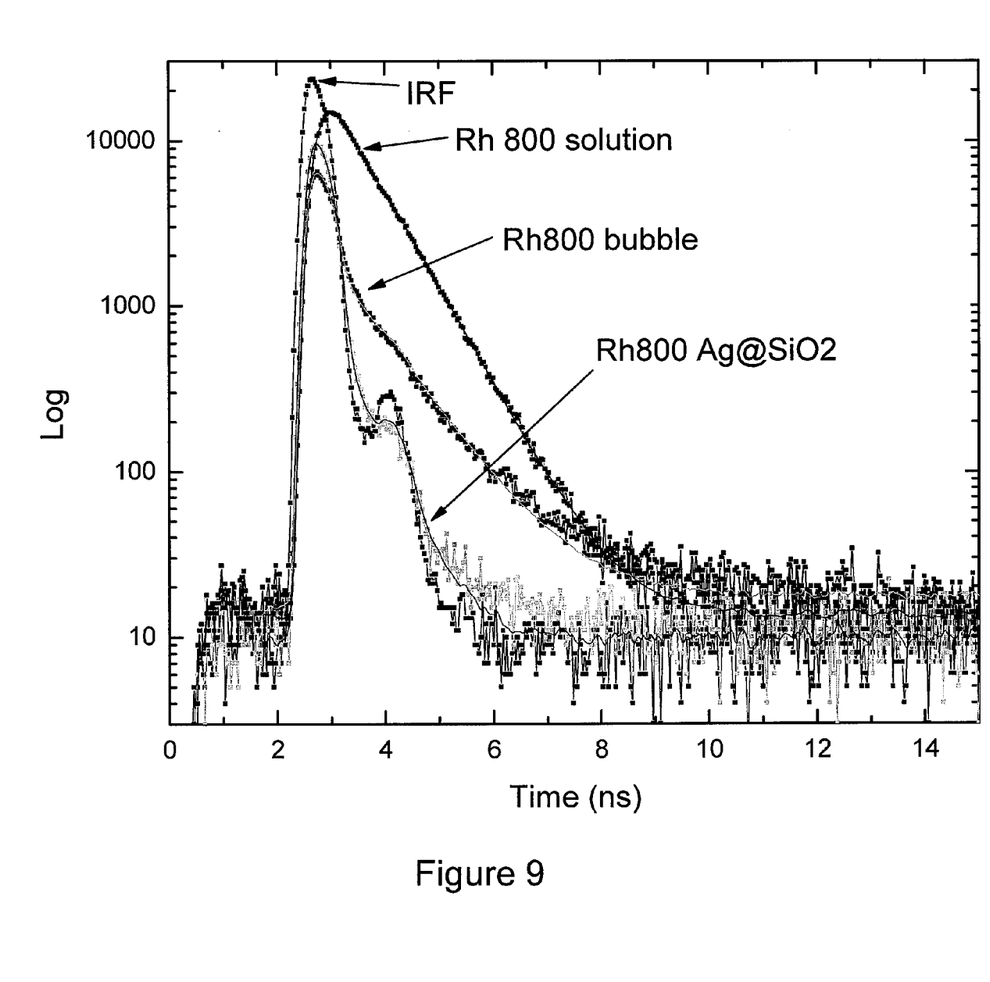
FIG. 9 shows the intensity time decay of Rh800 in solution, Rh800-doped Ag@$SiO_2$ and Rh800-doped $SiO_2$. The instrument response function (IRF), is also included.

It was observed that fluorescent core-shell nanoparticles, Rh800 $Ag@SiO_2$, have a faster decay (0.093 ns) than the corresponding nanobubbles (0.447 ns) and the fluorophore in solution (0.728 ns), (see FIG. 9 and Table 2 set forth below).

TABLE 2

|  | $\tau_1$ (μs) | $A_1$ % | $\tau_2$ (μs) | $A_2$ % | $\tau_{av}$ | $\chi^2$ |
|---|---|---|---|---|---|---|
| Rh800 in solution | 0.728 | 100 | — | — | 0.728 | 1.178 |
| Rh800 $Ag@SiO_2$ | 0.05 | 99.2 | 0.562 | 0.8 | 0.093 | 1.484 |
| Rh800 nanobubble | 0.04 | 96.5 | 0.954 | 3.5 | 0.447 | 1.759 |
| Alexa 647 Solution | 0.26 | 20.7 | 1.10 | 79.3 | 1.050 | 1.396 |
| Alexa 647 $Ag@SiO_2$ | 0.31 | 474.3 | 0.995 | 135.3 | 0.640 | 0.942 |
| Alexa 647 nanobubble | 1.73 | 100 | — | — | 1.730 | 1.023 |

The lifetimes of EuTDPA@Ag@SiO2 and EuTDPA@Nanobubble and in aqueous solution were measured to have an average lifetime of 25.3, 17.2, 2085 μs, respectively.

The average lifetimes of Alexa 647-linked $Ag@SiO_2$, the corresponding Alexa 647 nanobubble, and Alexa 647 in the aqueous solution were 0.64, 1.73, and 1.05 ns, respectively. These observations are in accordance with the previously described MEF phenomenon, [1,4,10,12] where the metal-fluorophore interactions result in an increase in the quantum yield (i.e., emission intensity) of the fluorophore and a decrease in the lifetime of fluorophores owing to two phenomena: an enhanced local electric field and an increase in the intrinsic system decay rate. The first factor provides stronger excitation rates but does not modify the fluorescence lifetime of the molecules. The second factor increases the net nanoparticle quantum yield.

It is interesting to comment on the total detectability of the new MEF nanoparticles, as this is paramount in microscopy and in single molecule studies. While a 20-fold increase in fluorescence/luminescence intensity is clearly beneficial, a reduced particle lifetime also enables the particle to be cycled faster, as the lifetime of a species determines its cyclic rate. Hence, 20-fold increase in intensity coupled with a 10-fold reduction in fluorophore-particle lifetime, provides for a ~200-fold potential increase in particle detectability. In addition, a reduced lifetime, affords for increased fluorophore photostability, as there is less time for excited state photodestructive processes to occur.

Figure 7:
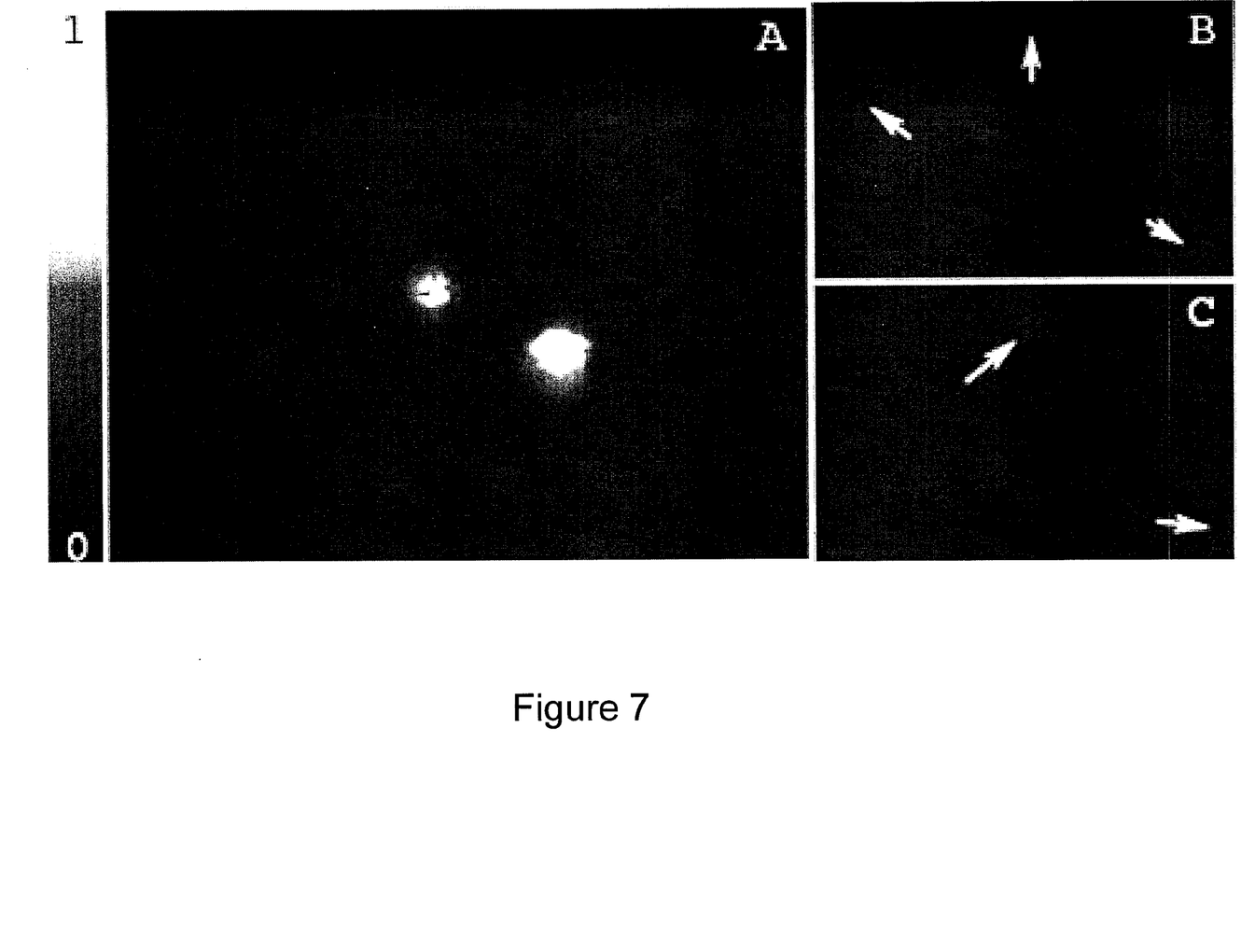
FIG. 7 shows scanning confocal images (20 um×20 um) of (A) Alexa 647 Ag@$SiO_2$, (B) Alexa 647@$SiO_2$, (C) zoomed in version of that shown in panel B. Intensity counts in the scale were normalized to 1.

FIG. 7 shows representative scanning confocal images of individual fluorescent core-shell nanoparticles, Alexa 647 $Ag@SiO_2$ (covalently linked), and the corresponding nanobubbles, Alexa $647@SiO_2$. The bright spots in FIG. 7a represent fluorescence emission from the single fluorescent core-shell nanoparticles, while the dimmer spots in FIG. 7b,c represent the single nanobubbles. The significant differences in the peak intensities of the two images are immediately evident from FIG. 7. For fluorescent core-shell nanoparticles the average value of the peak intensity was approximately 10-fold higher than that of the nanobubbles. This shows that using a silver core results in 10-fold enhancement in the fluorescence emission, which is attributed to the MEF phenomenon.[13] The heterogeneity in the spots' brightness (FIG. 7a) is due to the presence of nanobubbles in the same sample as fluorescent core-shell nanoparticles which were not completely separated after the preparation.

It is understood that the metal-enhanced fluorescence nanoparticles of the present invention can be used in multiple application including:

- Label in immunoassays, as a fluorescent label in flow cytometry, or a high intensity particle for single molecule assays and counting.
- A particle which can enhance the color or luminescence of cosmetics, surface coating, paints, inks and dye stuffs. For example, printing dyes for printers, hair color dyes, pigments for cosmetics (eye liner, Skin, etc), as intense color pigments for banknotes and as an anti counterfeiting measure.
- A particle which can enhance color by its absorption properties as compared to its emission properties. For example, a particle which absorbs heavily in the red and can be further enhanced, may show deeper colors in other regions of the spectrum.
- A particle which can be used to both deliver heat as well as used for simultaneous optical imaging.
- The particles can be made of metals that maintain a surface plasmon resonance or high free electron density.
- The particles can be used with different wavelengths of light and are not restricted to visible wavelengths, e.g. Infrared, Microwave frequencies etc.
- The particles could contain fluorescent ratiometric dyes for ratiometric type sensing, both absorption and emission based.
- The MEF nanoparticles can be used as sensing platforms, for particle surface DNA/RNA, enzyme and protein interactions and/or detection.
- Several fluorophores/luminophores can used in conjunction with the coatings for multiplexed assays or even digital counting assays, flow assays. The multiplexed assays can offer multicolor and multi lifetime opportunities for both sensing and imaging.
- The particles can be used to enhance singlet oxygen production.
- The particles can be used to enhance superoxide formation.
- The MEF nanoparticles can be used as multiphoton probes, for 2-5 photon microscopy, imaging applications.
- The MEF nanoparticles can be used with phosphorescence species, to enhance phosphorescence signatures or even phosphorescence photophysical properties.
- The MEF nanoparticles can contain triplet absorbers for direct enhanced triplet absorption.
- The MEF nanoparticles can contain species that show higher singlet and triplet state emission, for further enhanced spectral properties. For example, the Azulene molecule for $S_2$ states and Malachite Green for simultaneous $S_1$ and $S_2$ absorption and emission.
- The MEF nanoballs may be doped with species for enhanced triplet assays, e.g. photodynamic therapy.

Although the invention has been described with respect to specific embodiments, the details are not to be construed as limitations, for it will become apparent that various embodiments, changes and modifications may be resorted to without departing from the spirit and scope thereof, and it is understood that such equivalent embodiments are intended to be included within the scope of this invention.

References

The contents of all references cited herein are incorporated by reference herein for all purposes.

1. Aslan K, Gryczynski I, Malicka J, Matveeva E, Lakowicz J R, Geddes C D (2005) Metal-enhanced fluorescence: an emerging tool in biotechnology. *Curr Opin Biotechnol* 16(1):55-62.
2. Geddes C D, Aslan K, Gryczynski I, Malicka J, Lakowicz J R, Noble Metal (2005) Nanostructure for metal-enhanced fluorescence. In: Review Chapter for Geddes C D, Aslan K, Gryczynski I, Malicka J, Lakowicz J R (eds) Radiative decay engineering, In topics in fluorescence in fluorescence spectroscopy. Kluwer Academic/Plenum Publishers, New York, USA, p 405.
3. Malicka J, Gryczynski I, Kusba J, Lakowicz J R (2003) Effects of metallic silver island films on resonance energy transfer between Cy3 and Cy5-labeled DNA. *Biopolymers* 70:595-603.
4. Aslan K, Geddes C D (2005) Microwave-accelerated metal-enhanced fluorescence (MAMEF): A new platform technology for ultra-fast and ultra-bright assays. *Anal Chem* 77(24):8057-8067.
5. Aslan K, Huang J, Wilson G M, Geddes C D (2006) Metal-enhanced fluorescence-based RNA sensing. *J Am Chem Soc* 128:4206-4207.
6. Aslan K, Geddes C D (2006) Microwave-accelerated and metal-enhanced fluorescence myoglobin detection on silvered surfaces: Potential application to myocardial infarction diagnosis. *Plasmonics* 1(1):53-59.
7. Aslan K, Badugu R, Lakowicz J R, Geddes C D (2005) Metal-enhanced fluorescence from plastic substrates. *J Fluores* 15(2):99-104.
8. Aslan K, Holley P, Geddes C D (2006) Metal-enhanced fluorescence from silver nanoparticle-deposited polycarbonate substrates. *J Mater Chem* 16(27):2846-2857.
9. Geddes C D, Parfenov A, Roll D, Fang J, Lakowicz J R (2003) Electrochemical and laser deposition of silver for use in metal-enhanced fluorescence. *Langmuir* 19(15):6236-6241.
10. Aslan K, Szmacinski H, Lakowicz J R, Geddes C D (2004) Metal-enhanced fluorescence solution-based sensing platform. *J Fluores* 14:677-679.
11. Geddes C D (2002) Optical halide sensing using fluorescence quenching: Theory, simulations and applications—a review. *Meas Sci Tech* 12:R53-R88.
12. Aslan K, Leonenko Z, Lakowicz J R, Geddes C D (2005) Annealed silver-island films for applications in metal-enhanced fluorescence: Interpretation in terms of radiating plasmons. *J Fluores* 15:643-654.
13. Kobayashi Y, Katakami H, Mine E, Nagao D, Konno M, Liz-Marzan L M (2005) Silica coating of silver nanoparticles using a modified Stober method. *J Coll Inter Sci* 283(2):392-396.
14. Bruchez, M., Jr.; Moronne, M.; Gin, P.; Weiss, S.; Alivisatos, A. P. *Science* 1998, 281, 2013-2016.
15. Michalet, X.; Pinaud, F.; Lacoste, T. D.; Dahan, M.; Bruchez, M. P.; Alivisatos, A. P.; Weiss, S. *Single Mol.* 2001, 2, 261.

That which is claimed is:

1. A nanoparticle comprising a metallic core with a coating of a metal oxide wherein the metal oxide is silicon dioxide encompassing the metallic core, wherein the coating of metal oxide comprises excitable and radiative molecules impregnated therein, and wherein the excitable and radiative molecules are positioned from 5 nm to 50 nm from the metallic core to enhance emissions when excited by electromagnetic energy, wherein the excitable and radiative molecules are selected from the group consisting of a fluorophore and luminophore species.

2. The nanoparticle of claim 1, wherein the electromagnetic energy is in the UV to IR range.

3. The nanoparticle of claim 1, wherein the electromagnetic energy is in the visible range.

4. The nanoparticle of claim 1, wherein the coating of the metal oxide is evenly distributed on the metallic core having a thickness from about 5 nm to about 50 nm.

5. The nanoparticle of claim 1, wherein the metallic core has a diameter ranging from about 50 to 130 nm in diameter.

6. The nanoparticle of claim 1, wherein the metallic core comprises silver, gold, platinum, aluminum, copper, zinc, palladium and composites thereof.

7. The nanoparticle of claim 1, further comprising at least one targeting moiety, attached to the surface of the metal oxide containing coating, wherein the target moiety is specific for a specific marker.

8. The nanoparticle of claim 7, further comprising a linker for binding the targeting moiety to the surface of the coating the metal oxide, wherein the linker is selected from the group consisting of a lipid, a carbohydrate, a polysaccharide, a protein, a polymer, a glycoprotein, and a glycolipid.

9. The nanoparticle of claim 1, wherein the metallic core is a geometric shape including spherical, elliptical, triangular, or rod shape.

10. The nanoparticle of claim 1, further comprising a solution for dispersing the nanoparticle therein.

11. The nanoparticle of claim 10, wherein the solution is used in velocimetry of turbulent flows including liquids, gas, liquid crystals, super cooled liquids and plasmas.

12. A nanoparticle comprising a metallic core with a coating of a metal oxide wherein the metal oxide is silicon dioxide encompassing the metallic core, wherein the coating of the silicon dioxide comprises a fluorophore or luminophore species impregnated therein, and wherein the fluorophore or luminophore species is positioned from 5 nm to 50 nm from the metallic core to enhance emissions from the fluorophore or luminophore species when excited by electromagnetic energy.

13. A composition comprising the nanoparticle of claim 1.

* * * * *